(12) United States Patent
Wu (10) Patent No.: US 8,883,230 B2
(45) Date of Patent: Nov. 11, 2014

(54) USE OF BLACK SOYBEAN FOR TREATING OPHTHALMIC DISEASES

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 1167 days.

(21) Appl. No.: 12/036,565

(22) Filed: Feb. 25, 2008

(65) Prior Publication Data

US 2009/0214681 A1    Aug. 27, 2009

(51) Int. Cl.
*A61K 36/00* (2006.01)
*A61K 36/48* (2006.01)

(52) U.S. Cl.
CPC .................................. *A61K 36/48* (2013.01)
USPC .......................................... 424/757; 424/725

(58) Field of Classification Search
None
See application file for complete search history.

(56) References Cited

U.S. PATENT DOCUMENTS 6,001,368 A * 12/1999 Jenks ............................... 62/646
2008/0145482 A1* 6/2008 Li et al. .......................... 426/46

FOREIGN PATENT DOCUMENTS

| JP | 2005-261237 | 9/2005 |
|---|---|---|
| WO | WO2005/077176 | 8/2005 |
| WO | WO2007/023774 | 3/2007 |

OTHER PUBLICATIONS

Sakimoto, The effect with black soybean hull extract on ocular function, Food Style 21 (2004), 8 (10): 73-75.*
Jang et al., Anthocyanins protect against A2E phytooxidation and membrane permeabilization in retinal pigment epithelial cells, Phytochemistry and Photobiology, 2005, 81: 529-536.*
Oh et al, Isoflavone supplements exert hormonal and antioxidant effects in postmenopausal Korean women with diabetic retinopathy, Journal of medicinal food, (2005 Spring) vol. 8, No. 1, pp. 1-7.*
Lee et al, Recovery of aglycone of daidzein and genistein in soybeans, Hwahak Konghak (2005), 43(5), 641-645.*
Kim et al, Comparison of isoflavones composition in seed, embryo, cotyledon and seed coat of cooked-with-rice and vegetable soybean (*Glycine max* L.) varieties, Food chemistry, 2007 vol. 102, issue 3 p. 738-744.*
Gijzen et al, A class I chitinase from soybean seed coat, Journal of experimental botany, (Dec. 2001) vol. 52, No. 365, pp. 2283-2289.*
Feher J. et al., *Neurobiology of Aging*, 27(7):983-93, 2006.
Imamura Y. et al., *Proceedings of the National Academy of Sciences of the United States of America*, 103(30):11282-7, 2006.
Lee J.J. et al., *Investigative Ophthalmology & Visual Science*, 43(9):3117-24, 2002.
Mayerson and Hall, *The Journal of Cell Biology*, vol. 103:299-308, 1986.
Tabandeh et al., *Retina*., 26(9):1063-9, 2006.
Takahashi. R et al, *J Agric Food Chem*., Jun 1;53(11):4578-82, 2005.
Thom W. Mittag et al., *Exp Eye Res*., 69:677-683, 1999.
Wenzel et al., *Progress in Retinal and Eye Research* 24: 275-306, 2005.
Zarbin M.A., *Archives of Ophthalmology*, 122(4):598-614, 2004.
Zayit-Soudry et al., *Survey of Ophthalmology*,52(3):227-43, 2007.
Zhou Jr et al., *Cancer Res*. 15;58(22):5231-81999,1998.
Choung et al., "Isolation and Determination of Anthocyanins in Seed Coats of Black Soybean (*Glycine max* (L.) Merr.)," J. Agric. Food Chem., vol. 49:5848-5851 (2001) [Abstract].

* cited by examiner

*Primary Examiner* — Qiuwen Mi
(74) *Attorney, Agent, or Firm* — Volpe and Koenig, P.C.

(57) ABSTRACT

A method for treating a disease or disorder associated with retinal pigment epithelium (RPE) disturbance, comprising administering to a human in need thereof an effective amount of a black soybean (*Glycine max* (L.) Merr) product is provided, wherein the black soybean product is the seed coats of black soybean or an alcoholic extract of black soybean or seed coats thereof.

4 Claims, 8 Drawing Sheets

USE OF BLACK SOYBEAN FOR TREATING OPHTHALMIC DISEASES

BACKGROUND OF THE INVENTION

Black soybean (*Glycine max* (L.) Merr), a type of soybean with a black seed coat, has long been used as a health food and herb in Chinese traditional medicine, and the medicinal effects therefore have been studied for years. Some Chinese medical codices have disclosed that the black bean could be provided as detoxifier, anti-inflammatory drug and blood nutrient.

Specifically, black soybean phytochemicals inhibited the growth of transplantable human bladder carcinoma and tumor angiogenesis in mice (Zhou J R et al., *Cancer Res.* 58(22):5231-81999, 1998); and black soybean, displaying an antioxidant activity, reduced low density lipoprotein oxidation, which might play a crucial role in the prevention of oxidation-relative diseases (Takahashi. R et al, *J Agric Food Chem.*, 53(11):4578-82, 2005).

Retinal pigment epithelium (RPE) is a monolayer cell at the surface layer of the retina, which are located between the Bruch's membrane and the photoreceptors. The villous processes at the top of RPE are connected to the outer segments of the photoreceptors, and the basal infoldings at the bottom of RPE are connected to the choroids via the Bruch' membrane. Since the RPE can effectively remove or transmit the toxic materials and the metabolite of the choroid coat and the retina, the RPE form a blood-retinal barrier. In addition, the RPE has many functions, such as receiving light, phagocytizing the outer segments separated from the rod cell and the cone cell because of light stimulation, catabolizing the phagosome, synthesizing the extracellular matrix and the melanin, detoxifying the medicine, providing the essential material for reproducing the outer segments of the photoreceptor, storing and transmitting the Vitamin A, synthesizing the rhodospin, and forming the adherent force of the retina (Wenzel et al., *Progress in Retinal and Eye Research* 24: 275-306, 2005).

According to the statistics, a RPE of rat could remove 25000 outer segments separated from the rod cells and the cone cells because of light stimulation in one day, which obviously showed the importance of the frequent phagocytic metabolism (Mayerson and Hall, *The Journal of Cell Biology*, 103:299-308, 1986). The normal phagocytosis of the RPE plays a critical role in maintaining the health of the photoreceptors in the retina. Once the phagocytic ability of RPE is decreased, it will result in the degeneration of the photoreceptors (Wenzel et al., *Progress in Retinal and Eye Research* 24: 275-306, 2005). Therefore, to maintain the RPE function is quite important for the visional system. So far, there is no good treatment of a disease/disorder associated with RPE disturbance.

BRIEF SUMMARY OF THE INVENTION

The present invention is based on a discovery that a black soybean (*Glycine max* (L.) Merr) product has an unexpected efficacy in increasing RPE function, such as the phagocytic ability.

Accordingly, one aspect of the invention relates to a method for treating a disease or disorder associated with retinal pigment epithelium (RPE) disturbance, comprising administering to a human in need thereof an effective amount of a black soybean product. In an embodiment of the invention, the black soybean product is the seed coats of black soybean or an alcoholic extract of black soybean or seed coats thereof.

The other aspect of the invention relates to a method for increasing phagocytosis of RPE by treating the cells with an effective amount of the black soybean product as aforementioned.

The details of one or more embodiments of the invention are set forth in the description below. Other features or advantages of the present invention will be apparent from the following detailed description of several embodiments, and also from the appending claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

As used herein the following terms may be used for better interpretation of claims and specification.

The articles "a" and "an" are used herein to refer to one or more than one (i.e., at least one) of the grammatical object of the article. By way of example, "an element" means one element or more than one element.

The term "an alcoholic extract of black soybean" used herein refers to an extract prepared by extracting black soybean or seed coats thereof with an alcohol-containing solvent, e.g., a solvent containing ethanol or methanol at a concentration of 10-100% (v/v).

The term "retinal pigment epithelium (RPE)" used herein refers to the pigment cell layer just outside the neurosensory retina that nourishes retinal visual cells, and is firmly attached to the underlying choroid and overlying retinal visual cells. The RPE is composed of a single layer of hexagonal cells that are densely packed with pigment granules and are responsible for the phagocytosis and digestion of the discard discs at turn over rate of approximately 30-100 discs each day.

The term "a disease or disorder associated with retinal pigment epithelium disturbance" used herein refers to the disease or disorder related to RPE dysfunctions, such as decreasing the phagocytic ability of RPE or isomerizing trans retinal. When RPE function is decreased or lost, retinal cells may apoptosis and detach from its underlying layer of support tissue, so as to lead to vision loss, blindness, retinal detachment or leakage of blood-retinal barrier (Martin L. Katz, *Arch Gerontol Geriatr.*, 34(3):359-70, 2002). The disorders associated with retinal pigment epithelium disturbance include but are not limited to retinal detachments, such as retinal pigment epithelium detachment (Tabandeh et al., *Retina.*, 26(9):1063-9, 2006; Zayit-Soudry et al., *Survey of Opthalmology*, 52(3):227-43, 2007), loss of visual function, and blood-retinal barrier leakage. In addition, the disturbance of RPE would result in various diseases, include but are not limited to proliferative vitreoretinopathy (Lee J. J. et al., *Investigative Ophthalmology & Visual Science*, 43(9):3117-24, 2002), age related macula degeneration (AMD) (Zarbin M. A., *Archives of Ophthalmology*, 122(4):598-614, 2004; Feher J. et al., *Neurobiology of Aging*, 27(7):983-93, 2006), retinitis pigmentosa, diabetic retinopathy, macular dystrophies, and choroidal neovascularization (Imamura Y. et al., *Proceedings of the National Academy of Sciences of the United States of America*, 103(30): 11282-7, 2006; Tabandeh H., et al., *Retina*, 26(9):1063-9, 2006).

The phrase "treating a disease/disorder associated with RPE disturbance" or "treatment of a disease/disorder associated with RPE disturbance" refers to the application or administration of the black soybean product described herein to a subject, who has a disease/disorder associated with RPE disturbance, a symptom of the disease/disorder, or a predisposition toward the disease/disorder, with the purpose to cure, heal, alleviate, relieve, alter, remedy, ameliorate, improve, or affect the disease/disorder, the symptoms of the disease/disorder, or the predisposition toward the disease/disorder.

The term "an effective amount" used herein refers to the amount of each active agent which, upon administration with one or more other active agents to a subject in need thereof, is required to confer therapeutic effect on the subject. The effective amounts vary, as recognized by those skilled in the art, depending on route of administration, excipient usage, and the co-usage with other active agents. According to the invention, the effective amount refers to the amount effective in increasing the function of retinal pigment epithelium.

The present invention provides a method for treating a disease or disorder associated with retinal pigment epithelium (RPE) disturbance, comprising administering to a human in need thereof an effective amount of a black soybean (*Glycine max* (L.) Merr) product. According to the invention, the black soybean product is the seed coats of black soybean, or an alcoholic extract of black soybeans or seed coats thereof. The black soybean product may be prepared by any method well known or commonly used in the art.

In one example of the invention, the black soybean product may be the seed coats of black soybean, for instance, the seed coats may be directly shelled from black soybean with a husker, and fragmented into small pieces.

According to an example of the invention, the black soybean product may be an alcoholic extract of black soybean or seed coats thereof. The alcoholic extract may be obtained with any standard or commonly used by those skilled in the art. For instance, the extract may be prepared by extracting black soybean or seed coats thereof with an alcohol-containing solvent, e.g., a solvent containing ethanol or methanol at a concentration of 10-100% (v/v). In a particular example, a black soybean extract is obtained by soaking black soybeans in an alcohol-containing solvent for a sufficient period of time under a suitable temperature, and then removing insoluble bean substances by, e.g., filtration, to produce a black soybean extract in liquid form. Optionally, the product may be further dried by, e.g., evaporation, to obtain a product in a dry form. The alcohol-containing solvent may be a solvent containing 10-100% (v/v) alcohol, and one or more other suitable solvents, e.g., water, ethanol or methanol. In an example of the invention, the alcohol-containing solvent is a solvent containing ethanol in water. More preferably, the solvent is at least 10% (v/v) ethanol in water, and most preferably 35% (v/v) ethanol in water. In a particular example of the invention, the extract was prepared by the process comprising the steps of (1) providing whole black soybeans or seed coats thereof, (2) extracting the whole beans or seed coats thereof with a solvent containing 35% (v/v) ethanol in water, (3) collecting the soluble fraction thus formed, and optionally (4) drying the collected soluble fraction.

According to the invention, it is unexpectedly found that the black soybean product is effective in increasing the function of retinal pigment epithelium, which was confirmed by the methods or models commonly used or well known in the art, such as in terms of an increase of the phagocytic ability of RPE as shown in Example 2 (Mayerson and Hall, *The Journal of Cell Biology*, 103:299-308, 1986), and the ability of restoring b-wave in a mouse model with ophthalmic defect as shown in Examples 3 and 4 of the specification (Thom W. Mittag et al., *Exp Eye Res.*, 69:677-683, 1999). Therefore, the invention provides a method for treating a disease or disorder associated with RPE disturbance comprising administering to a subject in need of the treatment an effective amount of the black soybean product as aforementioned.

The black soybean product according to the invention may be in a form of a food, a dietary composition or pharmaceutical composition. In one example, the black soybean product may be mixed with a pharmaceutically acceptable carrier or excipient, and optionally with another therapeutically active agent, to form a pharmaceutical composition. The carrier or excipient suitable for the pharmaceutical composition must be "acceptable" in the sense that it is compatible with the active ingredient of the composition (and preferably, capable of stabilizing the active ingredient) and not deleterious to the subject to be treated. Examples of the carriers include colloidal silicon oxide, magnesium stearate, cellulose, sodium lauryl sulfate, D&C Yellow #10, microcrystalline cellulose, mannitol, glucose, defatted milk powder, polyvinylpyrrolidone, and starch, or a combination thereof. The pharmaceutical composition may be in a variety of forms, such as tablet, capsule, powder, or liquid.

According to the invention, the above-mentioned composition may be administered via suitable routes, e.g., oral administration. A solid formulation for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. This solid formulation may be designed to be released in the intestine. For example, the composition is confined in a solid sub-unit or a capsule compartment that have respectively a matrix or a wall or a closure comprising an enteric polymer which dissolves or disperses at the pH of the small or large intestine to release the drug substance in the intestine.

In another example, the black soybean product described herein is a component of a food product or a food supplement (e.g., a nutrient supply or an herbal product). Such food products may be prepared by any standard or commonly used methods in the food industry.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Preparation of Black Soybean Products

The first black soybean product was prepared by shelling the whole black soybean by a husker, and fragmented into small pieces to obtain the seed coats of black soybean (BGSC).

The second black soybean product was prepared from whole black soybean by extracting 2 kg of whole black soybeans with 20 L of 35% (v/v) ethanol in water to obtain 104.15 g of an ethanolic extract (BG35E).

The third type of the black soybean product was prepared from the seed coats of black soybean by removing the seed coats of black soybeans by a mini testing husker, collecting the seed coats (in the amount of 1.05 kg), extracting the seed coats as resulted with 35% (v/v) ethanol in water to obtain 117.25 g of an crude extract (BGSC35E).

Example 2

Effects of Black Soybean Extracts (BG35E and BGSC35E) on Phagocytosis of RPE

Preparation of RPE

The fresh bovine eyes were collected from a slaughterhouse within 2-3 hr after slaughtering. The surfaces of the bovine eyes were sterilized with the tincture of iodine, and then were washed with the PBS (phosphate-buffer saline) buffer solution twice. After dissecting the bovine eyes and removing the lens, the vitreous body, and the retina in sequence, the dissected eyes were treated with 0.01% EDTA (ethylene diamine tetra-acetic acid, Sigma, USA) for 40 min and then 5% trypsin (Merck, Germany) for 15 min. Then, a single cell of RPE was obtained after slightly pressing the eyes with a tweezer with round tips and pipetting several times. The pipetted solution was placed within the DMEM (Dulbecco's Modified Eagle Media, Gibco (Gaithersburg, USA) containing 10% FCS (fetal calf serum, GIBCO (Gaithersburg, USA) and then were incubated in an incubator with a humidified atmosphere with 5% $CO_2$ at 37° C. The medium was replaced per 5-6 days till the cells reach the confluency. The cells were subcultured with a medium containing 0.05% trypsin and 0.02% EDTA. The major cells used for the bioactivity test are the fifth and the sixth generations of the cells.

Preparation of Rod Outer Segments (ROS)

Fresh bovine eyes were kept on ice and exposed under a light for 30 minutes after obtaining form the slaughterhouse. The surfaces of the bovine eyes were sterilized with the tincture of iodine, and then were washed with the Hank's buffer solution twice. After dissecting the bovine eyes and removing the lens, and the vitreous body in sequence, the retina were taken out and cut into pieces and then treated with 20 mM Tris-HCl containing 20% sucrose. The cell solution was stirred for 3 hrs at 4° C., and then filtered with filters of pore size of 300, 220, 110, 74, 53, and 10 mesh (Small Parts, Miami, USA), respectively. After counting the numbers of ROS, the ROS were aliquoted with a number of $1\times10^8$ ROS per vial, and the vials were stored at −20° C.

Preparation of Fluorescein Isothiocyanate-ROS (FITC-ROS)

The stored ROS solution was unfrozen, and the suspension was removed. The solution as resulted was mixed with 700 ml Borate buffer (pH 8.0) containing 10% sucrose, and then the FITC powder (Invitrogen, USA) at a rate of 1/1,000 weight of the ROS was added. The solution as resulted was stirred for 1.5 hrs at 4° C. The uncombined FITC that were not attached on the ROS was removed by washing with 20 mM Tris-acetate (pH 7.2) containing 20% sucrose. The ROS solution was then centrifuged for 10 minutes at 10,000 rpm. The relevant steps described above are repeated several times to obtain a pellet of FITC-ROS. Finally, the pellet was dissolved in the DMEM containing 2.5% sucrose.

Testing the Ability of Phagocytosis of RPE In Vitro

The RPE were set up at a concentration of $1\times10^4$ cells/ml and seeded into 96 well plates containing 10% FCS DMEM. After a 48-hour incubation, the cultured medium was replaced with 2% FCS DMEM followed by an addition of either 20 μl of BG35E or BGSC35E in the concentration of 0.1, 1, 10, or 100 μg/ml into each well, respectively. In addition, a well was added with 10% FCS as a positive control, and a blank well (added with 2% FCS) was used as a control. After one-day incubation, 20 μl of the FITC-ROS solution was added into each well and incubated for four hours. After the incubation, the supernatant was removed to obtain a pellet for each well. The pellet of each well was washed with 2.5% sucrose/PBS for several times. Then, the total (external and internal) ROS were counted by the Cyto-Fluorometer (Ex filter: 485/20 nm, Em filter 530/25 nm). In addition, the external adhering FITC-labeled ROS were removed by adding FluoroQuench Dye, followed by a determination of phagocytized ROS (ingestion phagocytosis).

Results

Figure 1:
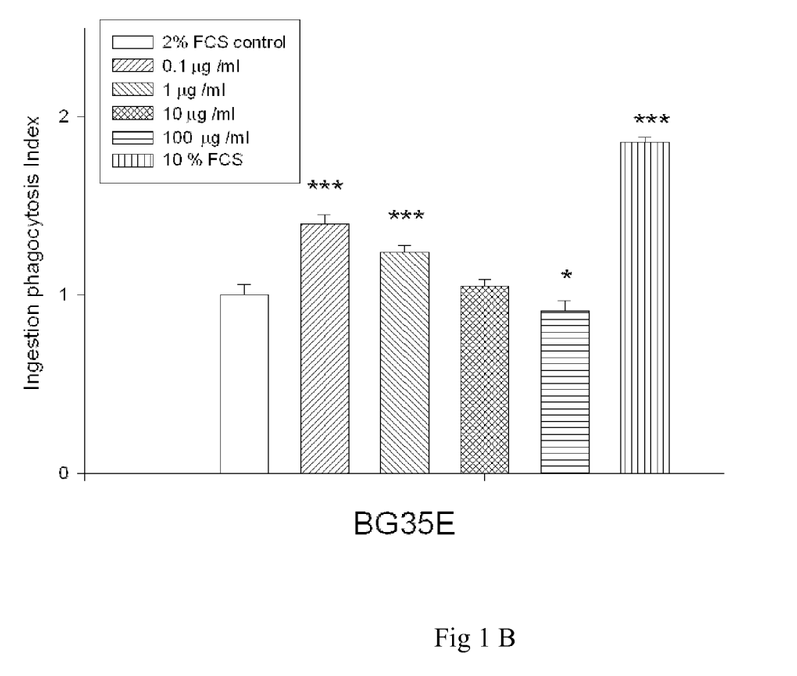
FIG. 1A and FIG. 1B are diagrams showing the effects of a black soybean extract on phagocytosis of RPE. The extract (BG35E) is prepared by extracting whole black soybean with 35% (v/v) ethanol. * indicates $P<0.05$;  indicates $P<0.01$; and * indicates $P<0.001$.
Figure 1A:
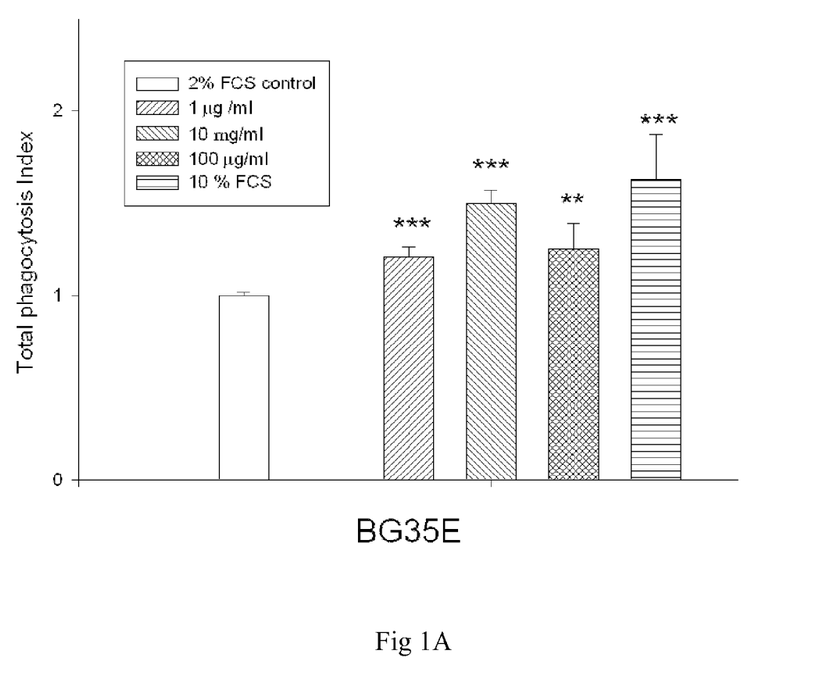

Referring to FIG. 1A, the total phagocytosis index in the ROS-FITC treated with 100 μg/ml of BG35E was higher by 25% than that treated with 2% FCS as a control. Meanwhile, the total phagocytosis index in the ROS-FITC treated with 10 μg/ml of BG35E was higher by 1.5 times than ROS-FITC treated with 2% FCS as a control. As shown in FIG. 1B, the ingestion phagocytosis index in the ROS-FITC treated with 1 μg/ml of BG35E was higher by 1.24 times than that treated with 2% FCS as a control. The ingestion phagocytosis index in the ROS-FITC treated with 0.1 μg/ml of BG35E was higher than that treated with 2% FCS as a control.

Figure 2:
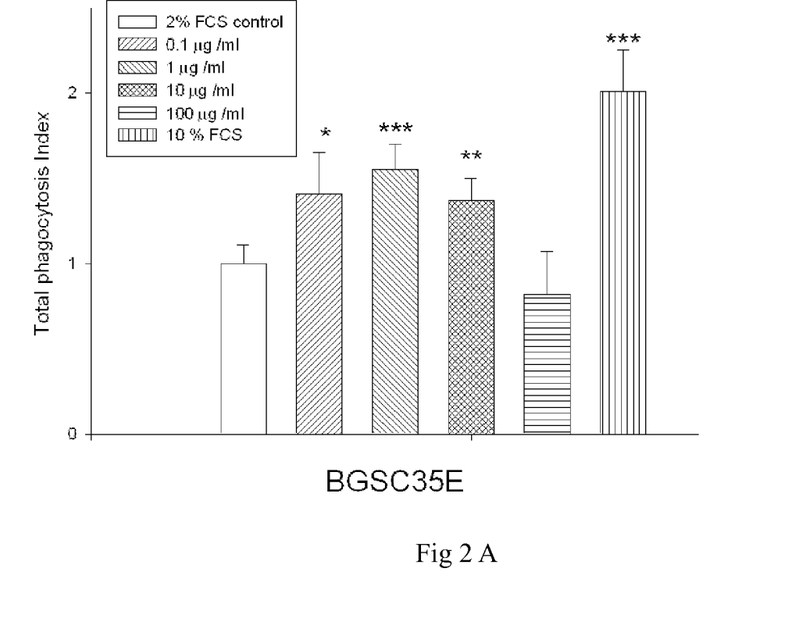
FIG. 2A and FIG. 2B are diagrams showing the effects of a black soybean extract on phagocytosis of RPE. The extract (BGSC35E) is prepared by extracting seed coats of black soybean with 35% (v/v) ethanol. * indicates $P \leq 0.05$;  indicates $P<0.01$; and * indicates $P<0.001$.
Figure 2B:
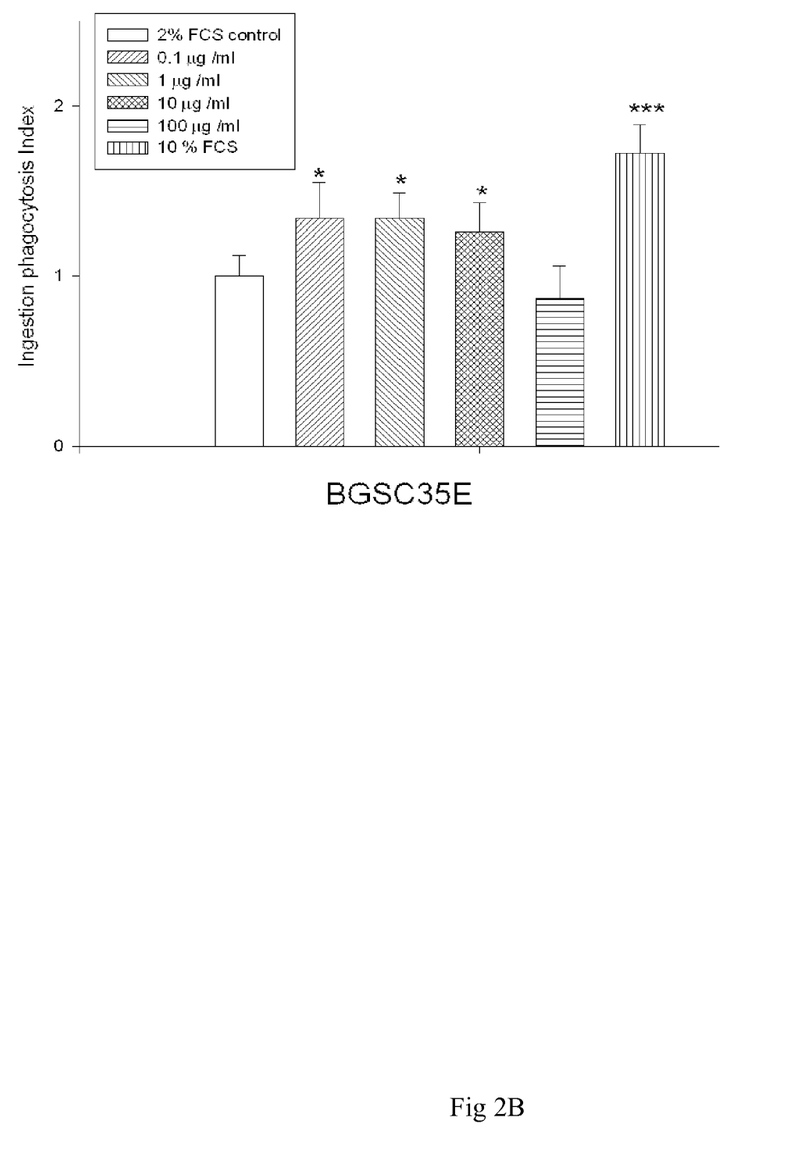

Referring to FIG. 2A, a similar result was found when the ROS-FITC were incubated with the extract of the seed coat of black soybean (BGSC35E). The total phagocytosis index in the ROS-FITC treated with 10 μg/ml of BGSC35E was higher by 1.37 times than that treated with 2% FCS. Further, the total phagocytosis index in the ROS-FITC treated with 1 μg/ml of BGSC35E was higher by 1.55 times than that treated with 2% FCS, as a control. Referring to FIG. 2B, the ingestion phagocytosis index in the ROS-FITC treated with 10 μg/ml of BGSC35E was higher by 1.26 times than that treated with 2% FCS as a control, and the ingestion phagocytosis index in the ROS-FITC treated with 1 μg/ml of BGSC35E was higher by 1.55 times than that treated with 2% FCS as a control. As a result, it was found in FIGS. 1 and 2 that after incubation with the extract of black soybean (BG35E) or with the extract of seed coat of black soybean (BGSC35E), the phagocytic ability of RPE was enhanced.

Example 3

Effect of Black Soybean Extract (BGSC35E) in Mouse Model with Ophthalmic Defect

Mouse Electroretinogram (ERG) Model

BALB/c male mice, aged 10 weeks, were randomly grouped into a normal group (healthy mice), a control group (damaged by light without a treatment of BGSC35E), a group treated with BGSC35E at a dose of 10 mg/kg body weight (BGSC35E 10 mg/kg), a group treated with BGSC35E at a dose of 40 mg/kg body weight (BGSC35E 40 mg/kg), or a group treated with BGSC35E at a dose of 160 mg/kg body weight (BGSC35E 160 mg/kg). Each group contained five mice and was provided with sufficient feed and water. The first day of the BGSC35E treatment was defined as Day 0. The a-wave and b-wave amplitudes were measured by ERG at Day −1, 1, 7, 13 and 19.

At Day −5, the mice that were responsive to light normally were selected for test. At Day −1, the mice were kept in dark for 24 hours. After the anesthesia with intraperitoneal avertin (400 mg/kg body weight), the mice were placed on a warming pad to maintain body temperature. The pupils were dilated with 1% cyclopentolate and anesthetized with 1% proparacaine. A gold wire loop electrode was placed on the cornea, and a gold wire differential electrode was placed on the tongue for each mouse. A reference electrode was attached to the head. The eyes of mice were exposed to 6 Volt of LED light, having a wave length from 500-575 nm, at the intensity of 5,000 lux for 1 msec. The a-wave and b-wave amplitudes of the mice were measured by ERG and recorded under a normal condition and after 2 hours of a light exposure.

Results

Figure 3A:
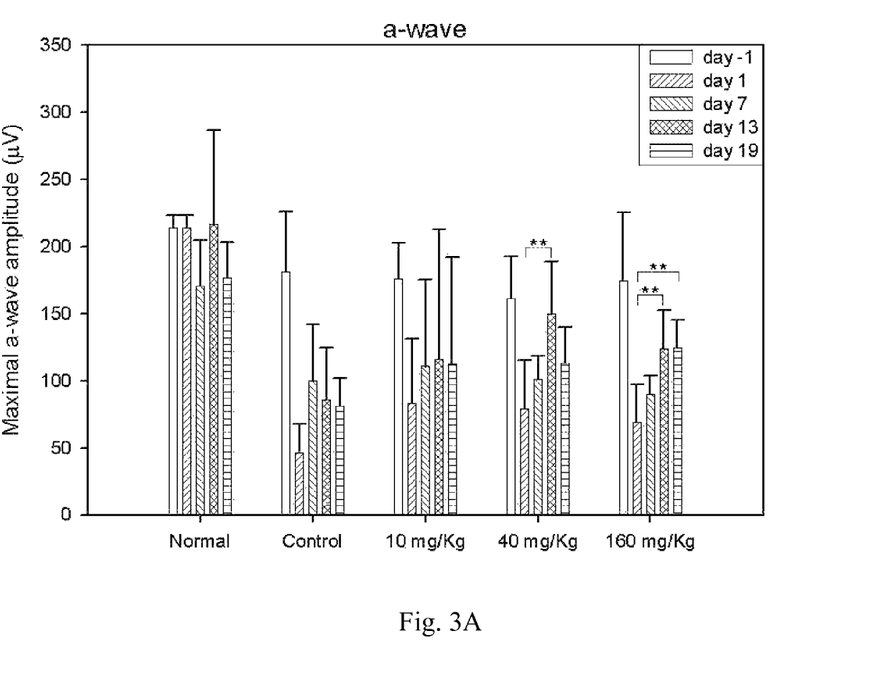
FIG. 3A and FIG. 3B are diagrams showing a-wave and b-wave, respectively, of ophthalmic defect mice treated with a black soybean extract (BGSC35E). The a-wave and b-wave are measured by Electroretinogram (ERG). * indicates $P<0.05$;  indicates $P<0.01$; and * indicates $P<0.001$.

Referring to FIG. 3A, it was found that the mice treated with BGSC35E at a dose of 40 mg/kg and those at a dose of 160 mg/kg had ability in restoring a-wave. The intensity values of a-wave of the mice treated with BGSC35E at a dose of 40 mg/kg or 160 mg/kg at Day 13 were found to be increased by more than 50% as compared with themselves at Day 1. The intensity values of a-wave of the mice treated with BGSC35E at a dose of 160 mg/kg at Day 19 were also found to be increased by more than 50% as compared with themselves at Day 1.

Figure 3B:
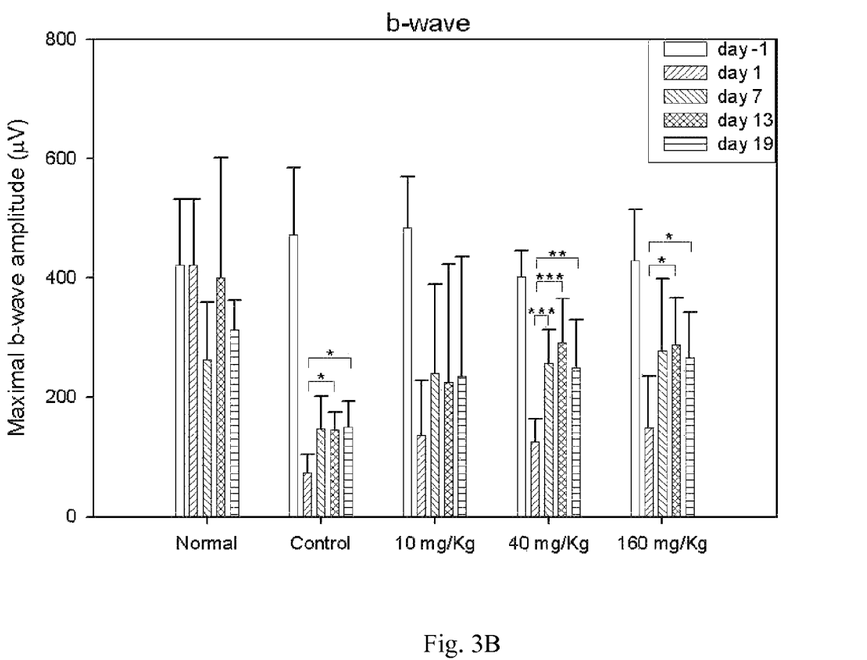

Referring to FIG. 3B, it was found that the control group and the mice treated with BGSC35E at a dose of 40 mg/kg and those at a dose of 160 mg/kg had ability in restoring b-wave. The intensity values of b-wave of the control group and the mice treated with BGSC35E at a dose of 40 mg/kg or 160 mg/kg at Day 13 and Day 19 were found to be increased as compared to themselves at Day 1. The intensity values of b-wave of the mice treated with BGSC35E at a dose of 40 mg/kg at Day 7 were also found to be significantly increased as compared with themselves at Day 1 ($p<0.001$). Given the above, the mice treated with BGSC35E had ability to restore abnormal ERG configuration, indicating that the BGSC35E provides an efficacy in increasing the RPE function, and could be used in the treatment of ophthalmic condition.

Example 4

Effect of the Seed Coats of Black Soybeans (BGSC) in Mouse Model with Ophthalmic Defect Mouse Electroretinogram (ERG) Model BALB/c male mice, aged 10 weeks, were randomly grouped into a normal group (healthy mice), a control group (damaged by light without a treatment of BGSC), a group treated with BGSC at a dose of 80 mg/kg body weight (BGSC 80 mg/kg) or a group treated with BGSC at a dose of 250 mg/kg body weight (BGSC 250 mg/kg). Each group contained five mice and were provided with sufficient feed and water. The first day of the BGSC treatment was defined as Day 0. The b-wave amplitudes were measured by ERG at Day −5, 0 and 15.

At Day −5, the mice that were responsive to light normally were selected for test. At Day −1, the mice were kept in dark for 24 hours. After the anesthesia with intraperitoneal avertin (400 mg/kg body weight), the mice were placed on a warming pad to maintain body temperature. The pupils were dilated with 1% cyclopentolate and anesthetized with 1% proparacaine. A gold wire loop electrode was placed on the cornea, and a gold wire differential electrode was placed on the tongue for each mouse. A reference electrode was attached to the head. The eyes of mice were exposed to 6 Volt of LED light, having a wave length from 500-575 nm, at the intensity of 5,000 lux for 1 msec. The b-wave amplitudes of the mice were measured by ERG and recorded under a normal condition and after 2 hours of a light exposure.

Following the same protocol, the mice treated with BGSC at a dose of 40, 160 or 640 mg/kg body weight, a normal group and a control group was tested. The b-wave amplitudes of the mice were measured by ERG at Day −4, 2, 9 and 16.

Results

Figure 4A:
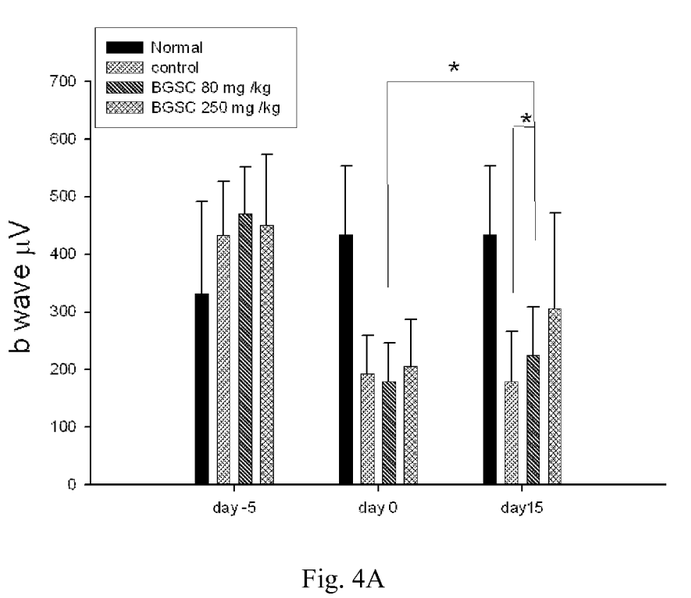
FIG. 4A and FIG. 4B are diagrams showing b-wave, respectively, of ophthalmic defect mice treated with a black soybean product made from the seed coats of black soybean (BGSC). The b-wave is measured by ERG. * indicates $P<0.05$;  indicates $P<0.01$; and * indicates $P<0.001$.

Referring to FIG. 4A, it was found that the mice treated with BGSC at a dose of 80 mg/kg and those at a dose of 250 mg/kg had ability in restoring b-wave. The intensity values of b-wave of the mice treated with BGSC at a dose of 80 mg/kg at Day 15 were found to be significantly increased as compared with themselves at Day 0 ($p<0.05$).

Figure 4B:
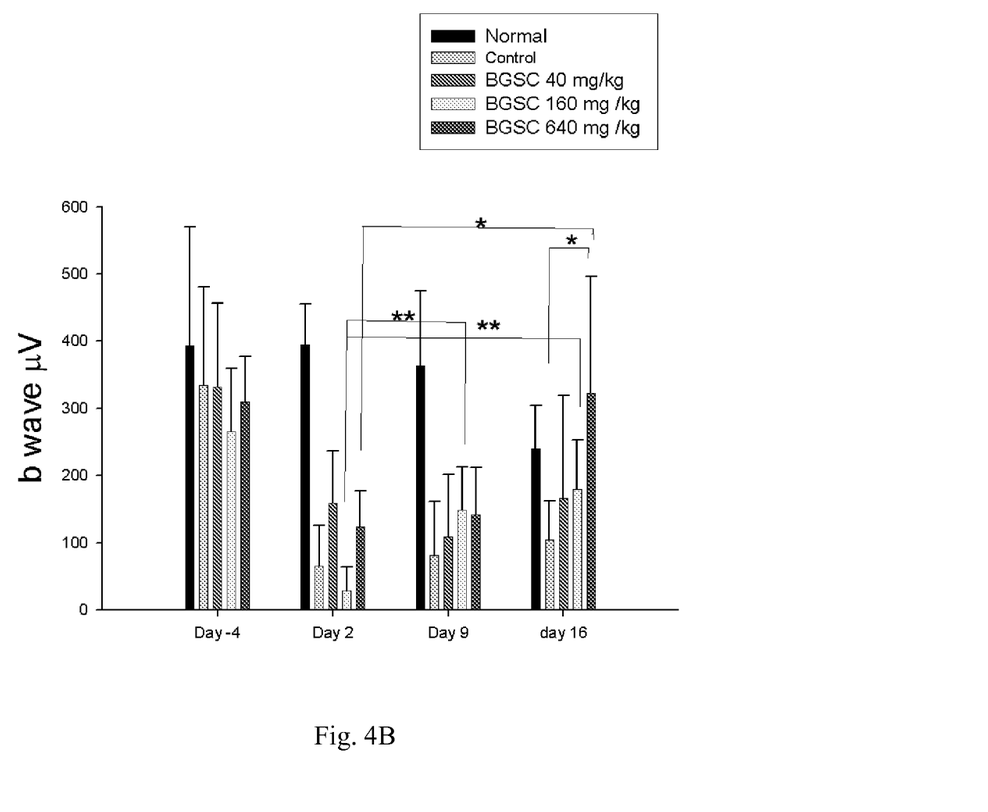

Referring to FIG. 4B, it is found that the mice treated with BGSC at a dose of 40 mg/kg, 160 mg/kg, or 640 mg/kg had ability in restoring b-wave. The intensity values of b-wave of the mice treated with BGSC at a dose of 160 mg/kg or 640 mg/kg at Day 9 and Day 16 were found to be increased as compared with themselves at Day 2. Given the above, the mice treated with BGSC had ability to restore abnormal ERG configuration, indicating that the BGSC provides an efficacy in increasing the RPE function, and could be used in the treatment of ophthalmic condition.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating a retinal pigment epithelium (RPE) disturbance by enhancing the function of RPE, comprising administering to a human in need thereof an effective amount of a black soybean product, wherein the black soybean product is seed coats of black soybean, or an ethanolic extract of seed coats of black soybean prepared by a process containing the following steps:
    (a) extracting seed coats of black soybean with an aqueous solution containing at least 35% (v/v) ethanol;
    (b) collecting the soluble fraction thus formed to obtain the ethanolic extract;
    wherein the black soybean product is effective in increasing the phagocytic ability of RPE, and wherein the RPE disturbance is one of a proliferative vitreoretinopathy, an age related macular degeneration, a retinitis pigmentosa, a macular dystrophy, or a choroidal neovascularization.

2. The method according to claim 1, wherein the black soybean product is in liquid form.

3. The method according to claim 1, wherein the black soybean product is in dry form.

4. The method according to claim 1, wherein the black soybean product is administered orally.

* * * * *